United States Patent
Zhao et al.

(10) Patent No.: US 8,795,181 B2
(45) Date of Patent: Aug. 5, 2014

(54) SYSTEM AND METHOD FOR ANALYZING CARPAL TUNNEL USING ULTRASOUND IMAGING

(75) Inventors: Chunfeng Zhao, Rochester, MN (US); Kai-Nan An, Rocheser, MN (US); Peter C. Amadio, Rochester, MN (US); Hector R. Villarraga, Rochester, MN (US); Yuichi Yoshii, Ibaragai (JP)

(73) Assignee: MAYO Foundation for Medical Education and Research, Rochester, MN (US)

( * ) Notice: Subject to any disclaimer, the term of this patent is extended or adjusted under 35 U.S.C. 154(b) by 169 days.

(21) Appl. No.: 13/130,210

(22) PCT Filed: Nov. 24, 2009

(86) PCT No.: PCT/US2009/065750
§ 371 (c)(1),
(2), (4) Date: May 19, 2011

(87) PCT Pub. No.: WO2010/068450
PCT Pub. Date: Jun. 17, 2010

(65) Prior Publication Data
US 2011/0237949 A1    Sep. 29, 2011

Related U.S. Application Data

(60) Provisional application No. 61/117,705, filed on Nov. 25, 2008.

(51) Int. Cl.
*A61B 8/00* (2006.01)
(52) U.S. Cl.
USPC .......................................... 600/453; 600/437

(58) Field of Classification Search
USPC .......... 600/437, 438, 441, 453, 447; 128/922, 128/923; 424/94.64
See application file for complete search history.

(56) References Cited

U.S. PATENT DOCUMENTS

| | | | |
|---|---|---|---|
| 5,031,640 A * | 7/1991 | Spitzer | 128/878 |
| 6,264,621 B1 | 7/2001 | Paske | |
| 2004/0082886 A1 | 4/2004 | Timpson | |
| 2006/0239540 A1 | 10/2006 | Serra et al. | |
| 2007/0167809 A1* | 7/2007 | Dala-Krishna | 600/459 |

(Continued)

FOREIGN PATENT DOCUMENTS

| WO | 0076400 A1 | 12/2000 |
|---|---|---|
| WO | 2007067987 A2 | 6/2007 |

OTHER PUBLICATIONS

International Search Report and Written Opinion under date of in connection with PCT/US2009/065750.

(Continued)

*Primary Examiner* — Long V. Le
*Assistant Examiner* — Lawrence Laryea
(74) *Attorney, Agent, or Firm* — Quarles & Brady, LLP

(57) ABSTRACT

A system and method is provided for using dynamic ultrasonic imaging to analyze a subject's carpal tunnel and generate risk factors indicative of the health of the subject's subsynovial connective tissue and the subject's risk of developing carpal tunnel syndrome. The system and method uses speckle imaging techniques to track dynamic structures within the carpal tunnel and statistical analysis techniques to compare the properties of these dynamic structures of the subject to those of normal subjects and subjects having carpal tunnel syndrome.

13 Claims, 6 Drawing Sheets

(56) References Cited

U.S. PATENT DOCUMENTS

| | | | |
|---|---|---|---|
| 2008/0009736 A1* | 1/2008 | Amadio et al. | 600/453 |
| 2008/0071165 A1* | 3/2008 | Makin et al. | 600/411 |
| 2010/0004540 A1* | 1/2010 | Thiele | 600/447 |

OTHER PUBLICATIONS

Gliding Characteristics between Flexor Tendons and Surrounding Tissues in the Carpal Tunnel: A Biomechanical Cadaver Study; Zhao; Wiley InterScience; DOI 10.1002 [jor. 20321].

Longitudinal Sliding of the Median Nerve in Patients with Carpal Tunnel Syndrome; Journal of Hand Surgery (British and European vol. 2003) 28B: 5: 439-443.

Relative Longitudinal Motion of hte Finger Flexors, Subsynovial Connective Tissue, and Median Nerve Before and After Carpal Tunnel Release in a Human Cadaver Model; Yamaguchi; JHS vol. 33A, Jul.-Aug. 2008.

Detection of Differential Gliding Characteristics of the Flexor Digitorum Superficialis Tendon and Subsynovial Connective Tissue Using Color Doppler Sonographic Imaging; Oh; J. Ultrasound Med 2007; 26: 149-155.

* cited by examiner

SYSTEM AND METHOD FOR ANALYZING CARPAL TUNNEL USING ULTRASOUND IMAGING

CROSS-REFERENCE TO RELATED APPLICATIONS

This application is based on, claims the benefit of, and incorporates herein by reference in their entirety, PCT International Application PCT/US2009/065750 filed on Nov. 24, 2009, which claims benefit of U.S. Provisional Patent Application Ser. No. 61/117,705, filed on Nov. 25, 2008, entitled "System and Method for Analyzing the Carpal Tunnel Using Ultrasound.

STATEMENT REGARDING FEDERALLY SPONSORED RESEARCH

This invention was made with government support under grant number AR049823, awarded by the National Institutes of Health. The government has certain rights in the invention.

FIELD OF THE INVENTION

The present invention relates to systems and methods ultrasonic imaging and, more particularly, to systems and methods for analyzing the health of structures within a subject's carpal tunnel using ultrasonic imaging methods.

BACKGROUND OF THE INVENTION

Carpal tunnel syndrome (CTS), which is a pressure induced neuropathy of the median nerve at the wrist, is a common clinical problem. The carpal tunnel is a sheath of tough connective tissue that protects and encloses a variety of structures, including the flexor tendons and the median nerve. Also within the carpal tunnel is the subsynovial connective tissue (SSCT), a specially adapted paratendon that mediates movement between the flexor tendons and the median nerve. The mechanical significance of the SSCT relates to its effect on the kinematics within the carpal tunnel and, as a framework for blood and lymph vessels, the SSCT plays a fundamental role in the nutrition of the structures embedded in it.

Studies have shown that SSCT motion characteristics and thickness differ between subjects with CTS and unaffected subjects. It is believed that an increased volume of the SSCT, especially if combined with altered transmission of tendon forces through the SSCT in the carpal tunnel, affects carpal tunnel pressure and therefore increases the likelihood of CTS.

Diagnostic ultrasonography has previously been used in confirming the diagnosis of CTS and in excluding other pathologies. Specifically, ultrasonography has been used to diagnose CTS, based on static images of nerve morphology. Static ultrasound imaging for CTS diagnosis can detect thickening and echogenicity alteration of the flexor tendons and flexor retinaculum, restricted median nerve sliding in the carpal tunnel, synovial proliferation, and flattening of the median nerve. However, static ultrasound imaging cannot assess dynamic features within the carpal tunnel, for example, tendon mechanics and pathomechanics. Thus, dynamic observations of the SSCT have traditionally required surgical exposure of the carpal tunnel and are not useful for the assessment of early changes in the SSCT in individuals affected by, or at risk for, CTS.

There are a number of modes in which ultrasound can be used to produce images of objects. For example in static, "B-scan," ultrasound imaging, the transducer transmits a series of ultrasonic pulses as it is scanned across the object along a single axis of motion. The resulting echo signals are recorded and their amplitude is used to modulate the brightness of pixels on a display. The location of the transducer and the time delay of the received echo signals locates the pixels to be illuminated. With this static method, enough data are acquired from which a two-dimensional image of the refractors can be reconstructed. Rather than physically moving the transducer over the subject to perform a scan it is more common to employ an array of transducer elements and electronically move an ultrasonic beam over a region in the subject.

Another example is Doppler ultrasound imaging. Doppler systems employ an ultrasonic beam to measure the velocity of moving reflectors, such as flowing blood cells. Blood velocity is detected by measuring the Doppler shifts in frequency imparted to ultrasound by reflection from moving red blood cells. Accuracy in detecting the Doppler shift at a particular point in the bloodstream depends on defining a small sample volume at the required location and then processing the echoes to extract the Doppler shifted frequencies.

A Doppler system is incorporated in a real time scanning imaging system. The system provides electronic steering and focusing of a single acoustic beam and enables small volumes to be illuminated anywhere in the field of view of the instrument, whose locations can be visually identified on a two-dimensional B-scan image. A Fourier transform processor faithfully computes the Doppler spectrum backscattered from the sampled volumes, and by averaging the spectral components the mean frequency shift can be obtained. Typically the calculated blood velocity is used to color code pixels in the B-scan image.

Doppler imaging has been attempted to be used for assessing tendon velocity and excursion for hand and wrist motions. However, tissue Doppler imaging is a one-dimensional method that can only quantify the axial component of motion in an angle dependent manner. Doppler measurements lose its validity when the angle between the ultrasonic beam and the tissue exceeds a certain range. As a result, static ultrasonography and tissue Doppler imaging cannot adequately assess the condition of the SSCT and a subject's risk of developing CTS.

It would therefore be desirable to develop a system and method for non-invasively analyzing the carpal tunnel, and the SSCT in particular, that could be used to generate risk factors indicative of a subject's risk of developing carpel tunnel syndrome or SSCT damage.

SUMMARY OF THE INVENTION

The present invention overcomes the aforementioned drawbacks by providing a system and method for analyzing the health of a subject's carpal tunnel without invasive analysis. Specifically, the present invention provides a system and method for performing ultrasound analysis of a subject's carpal tunnel by arranging a subject within an examination apparatus, acquiring a plurality of time series of ultrasound images of the subject's carpal tunnel as the subject performs a series of tasks controlled by the examination apparatus and performing speckle tracking on the time series of ultrasound images. The speckle tracking is then analyzed to determine a plurality of functional parameters of the subject and statistical analysis is performed to compare the functional parameters of the subject to a priori functional parameters from normal subjects and subjects having carpal tunnel syndrome. Thereby, risk factors indicative of the subject's risk of developing carpal tunnel syndrome or subsynovial connective tissue damage are generated.

In accordance with one aspect of the invention, a system is provided for generating a report indicating a subject's risk for developing a disorder of a carpal tunnel. The system includes an examination apparatus configured to control motion of the subject through a predetermined set of motions, an ultrasound transducer arranged proximate to the subject's carpel tunnel to acquire a time series of medical imaging data of a region of interest including at least a portion of the subject's carpel tunnel, and a processor configured to receive the time series of medial imaging data. The processor includes instructions configured to cause the processor to carry out the steps of generating a time series of images from the time series of medial imaging data and receiving an indication of anatomical features within the time series of medical images. The processor also carries out the steps of analyzing the time series of medical images to determine indicia of acoustic signals arising from coherent reflection of ultrasound waves generated by the transducer from predetermined features within the region of interest and track the determined indicia across the time series of medical images. Also, the processor carries out the steps of determining a pattern of motion of the determined indicia across the time series of medical images, generating a series of functional parameters characterizing pattern of motion of the determined indicia across the time series of medical images, and, using the series of functional parameters, generating a report indicating the subject's risk of developing at least one of carpal tunnel syndrome (CTS) and subsynovial connective tissue (SSCT) damage.

Various other features of the present invention will be made apparent from the following detailed description and the drawings.

DESCRIPTION OF THE PREFERRED EMBODIMENT

Figure 1:
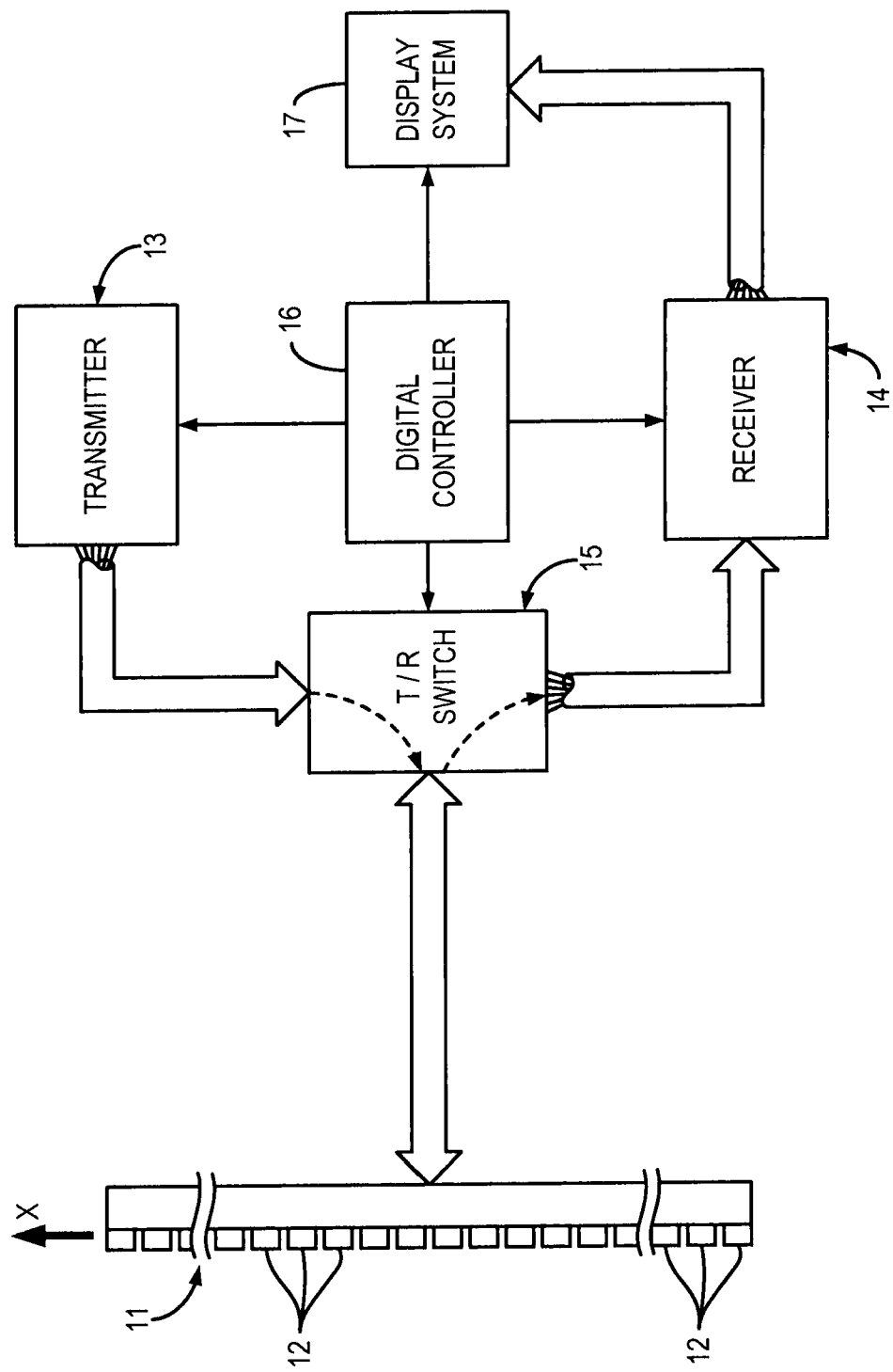
FIG. 1 is a block diagram of an ultrasonic imaging system configured to employs the present invention.

Referring to FIG. 1, an ultrasonic imaging system includes a transducer array 11 comprised of a plurality of separately driven elements 12 which each produce a burst of ultrasonic energy when energized by a pulse produced by a transmitter 13. The ultrasonic energy reflected back to the transducer array 11 from the subject under study is converted to an electrical signal by each transducer element 12 and applied separately to a receiver 14 through a set of switches 15. The transmitter 13, receiver 14 and the switches 15 are operated under the control of a digital controller 16 responsive to the commands input by the human operator. A complete scan is performed by acquiring a series of echoes in which the switches 15 are set to their transmit position, the transmitter 13 is gated on momentarily to energize each transducer element 12, the switches 15 are then set to their receive position, and the subsequent echo signals produced by each transducer element 12 are applied to the receiver 14. The separate echo signals from each transducer element 12 are combined in the receiver 14 to produce a single echo signal which is employed to produce a line in an image on a display system 17.

The display system 17 receives the series of data points produced by the receiver 14 and converts the data to a form producing the desired image. For example, if an A-scan is desired, the magnitude of the series of data points is merely graphed as a function of time. If a B-scan is desired, each data point in the series is used to control the brightness of a pixel in the image, and a scan comprised of a series of measurements at successive locations along the length of the transducer 11 (linear array mode) or steering angles (PASS mode) is performed to provide the data necessary for display.

Figure 2:
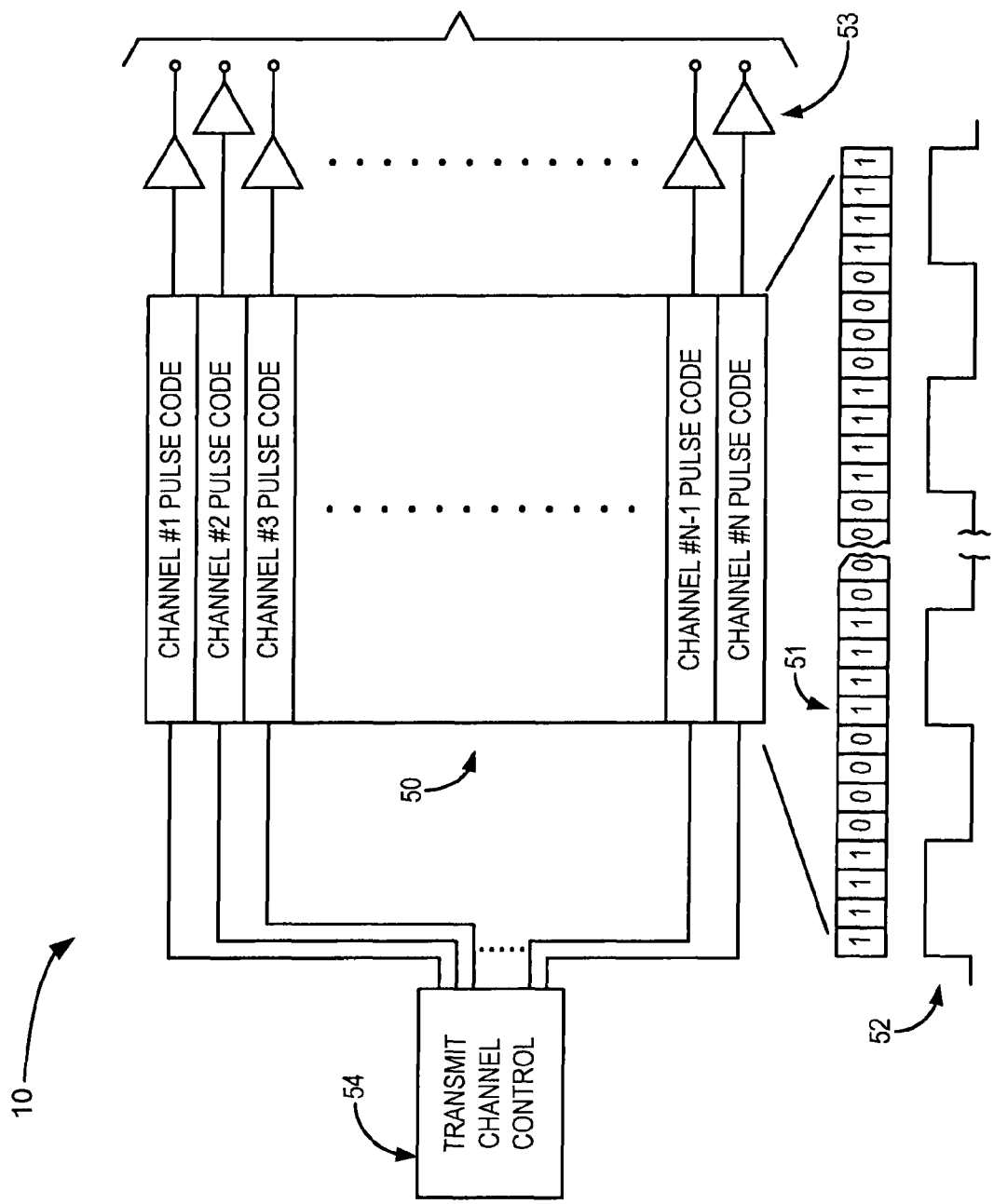
FIG. 2 is a block diagram of a transmitter that forms part of the system of FIG. 1.

Referring particularly to FIG. 2, the transmitter 13 includes a set of channel pulse code memories which are indicated collectively at 50. Each pulse code memory 50 stores a bit pattern 51 that determines the frequency of the ultrasonic pulse 52 that is to be produced. This bit pattern is read out of each pulse code memory 50 by a master clock and applied to a driver 53 which amplifies the signal to a power level suitable for driving the transducer 11. In the example shown in FIG. 2, the bit pattern is a sequence of four "1" bits alternated with four "0" bits to produce a 5 MHz ultrasonic pulse 52. The transducer elements 11 to which these ultrasonic pulses 52 are applied respond by producing ultrasonic energy.

As indicated above, to steer the transmitted beam of the ultrasonic energy in the desired manner, the pulses 52 for each of the N channels must be produced and delayed by the proper amount. These delays are provided by a transmit control 54 which receives control signals from the digital controller 16 of FIG. 1. When the control signal is received, the transmit control 54 gates a clock signal through to the first transmit channel 50. At each successive delay time interval thereafter, the clock signal is gated through to the next channel pulse code memory 50 until all the channels to be energized are producing their ultrasonic pulses 52. Each transmit channel 50 is reset after its entire bit pattern 51 has been transmitted and the transmitter 13 then waits for the next control signal from the digital controller 16.

Figure 3:
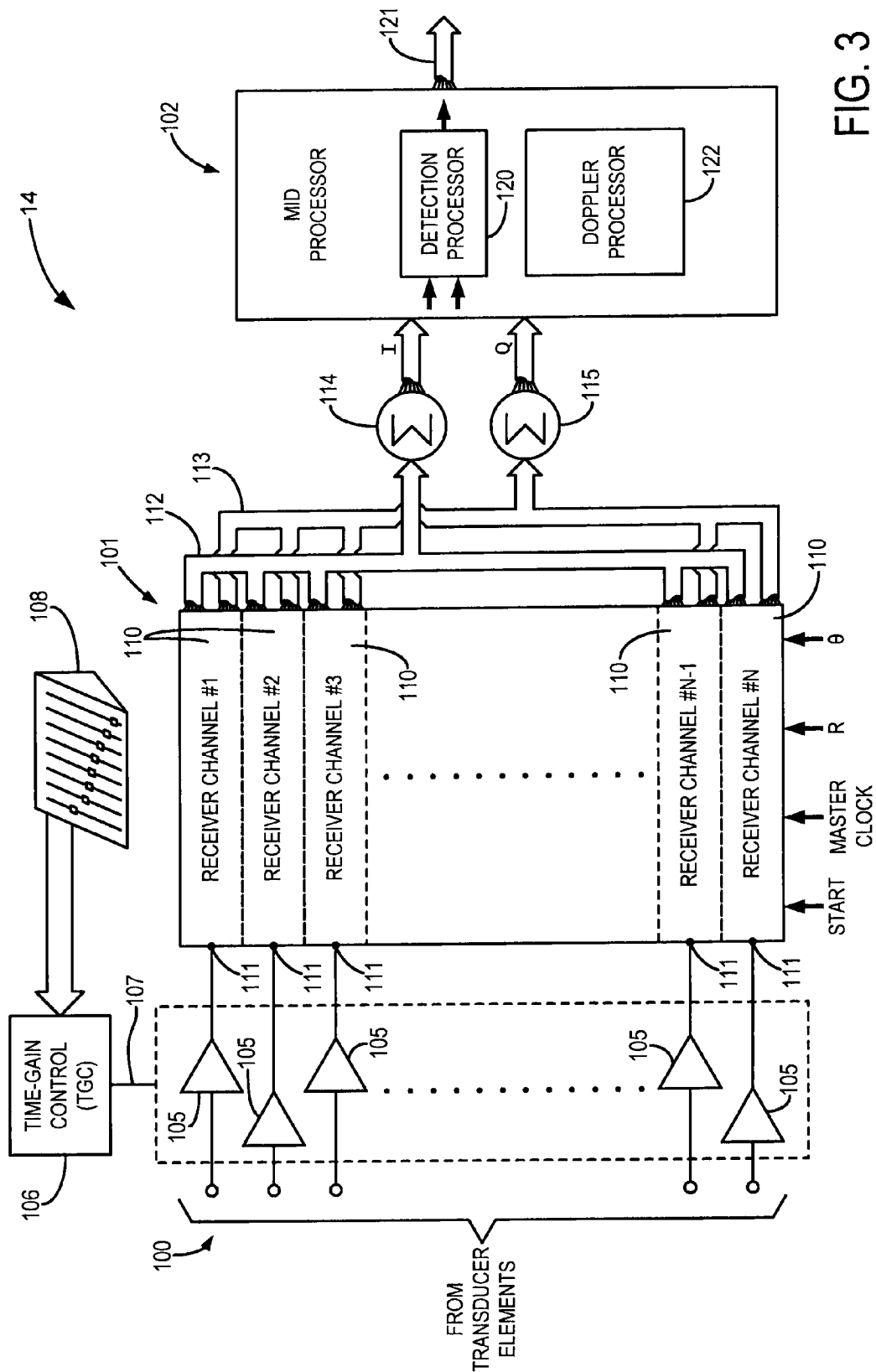
FIG. 3 is a block diagram of a receiver that forms part of the system of FIG. 1.

Referring particularly to FIG. 3, the receiver 14 is includes three primary sections including a time-gain control section 100, a beam forming section 101, and a mid processor 102. The time-gain control section 100 includes an amplifier 105 for each of the N receiver channels and a time-gain control circuit 106. The input of each amplifier 105 is connected to a respective one of the transducer elements 12 to receive and amplify the echo signal which it receives. The amount of amplification provided by the amplifiers 105 is controlled through a control line 107 that is driven by the time-gain control circuit 106. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range (R). This amplification is controlled by the operator who manually sets TGC linear potentiometers 108 to values which provide a relatively uniform brightness over the entire range of the scan. The time interval over which the echo signal is acquired determines the range from which it emanates, and this time interval is divided into segments by the TGC control circuit 106. The settings of the potentiometers are employed to set the gain of the amplifiers 105 during each of the respective time intervals so that the echo signal is amplified in ever increasing amounts over the acquisition time interval.

The beam forming section 101 of the receiver 14 includes N separate receiver channels 110. Each receiver channel 110 receives the analog echo signal from one of the TGC amplifiers 105 at an input 111, and it produces a stream of digitized output values on an I bus 112 and a Q bus 113. Each of these I and Q values represents a sample of the echo signal envelope at a specific range (R). These samples have been delayed in the manner described above such that when they are summed at summing points 114 and 115 with the I and Q samples from each of the other receiver channels 110, they indicate the magnitude and phase of the echo signal reflected from a point P located at range R on the ultrasonic beam.

Referring still to FIG. 3, the mid processor section 102 receives the beam samples from the summing points 114 and 115. The I and Q values of each beam sample is a digital number which represents the in-phase and quadrature components of the magnitude of the reflected sound from a point P. The mid processor 102 can perform a variety of calculations on these beam samples, where choice is determined by the type of image to be reconstructed. For example, if a conventional magnitude image is to be produced, a detection process indicated at 120 is implemented in which a digital magnitude M is calculated from each beam sample and output at 121.

$$M=\sqrt{I_2+Q_2}$$

The detection process 120 may also implement correction methods, for example, such as that disclosed in U.S. Pat. No. 4,835,689. Such correction methods examine the received beam samples and calculate corrective values that can be used in subsequent measurements by the transmitter 13 and receiver 14 to improve beam focusing and steering. Such corrections are desirable, for example, to account for the non-homogeneity of the media through which the sound from each transducer element travels during a scan.

The mid processor may also include a Doppler processor 122. Such Doppler processors often employ the phase information ($\phi$) contained in each beam sample to determine the velocity of reflecting objects along the direction of the beam (i.e. direction from the transducer 11), where $\phi=\tan^{-1}(I/Q)$.

The mid processor may also include a correlation flow processor 123, such as that described in U.S. Pat. No. 4,587,973, issued May 13, 1986 and entitled "Ultrasonic Method Can Means For Measuring Blood Flow And The Like Using Autocorrelation". Such methods measure the motion of reflectors by following the shift in their position between successive ultrasonic pulse measurements.

As appreciated by one of ordinary skill, the above-described system can be used to perform a number of imaging studies. In accordance with the present invention, the system may be designated to analyze the tissues of the carpal tunnel and generate risk factors indicative of a subject's risk of developing CTS or SSCT damage.

Figure 4:
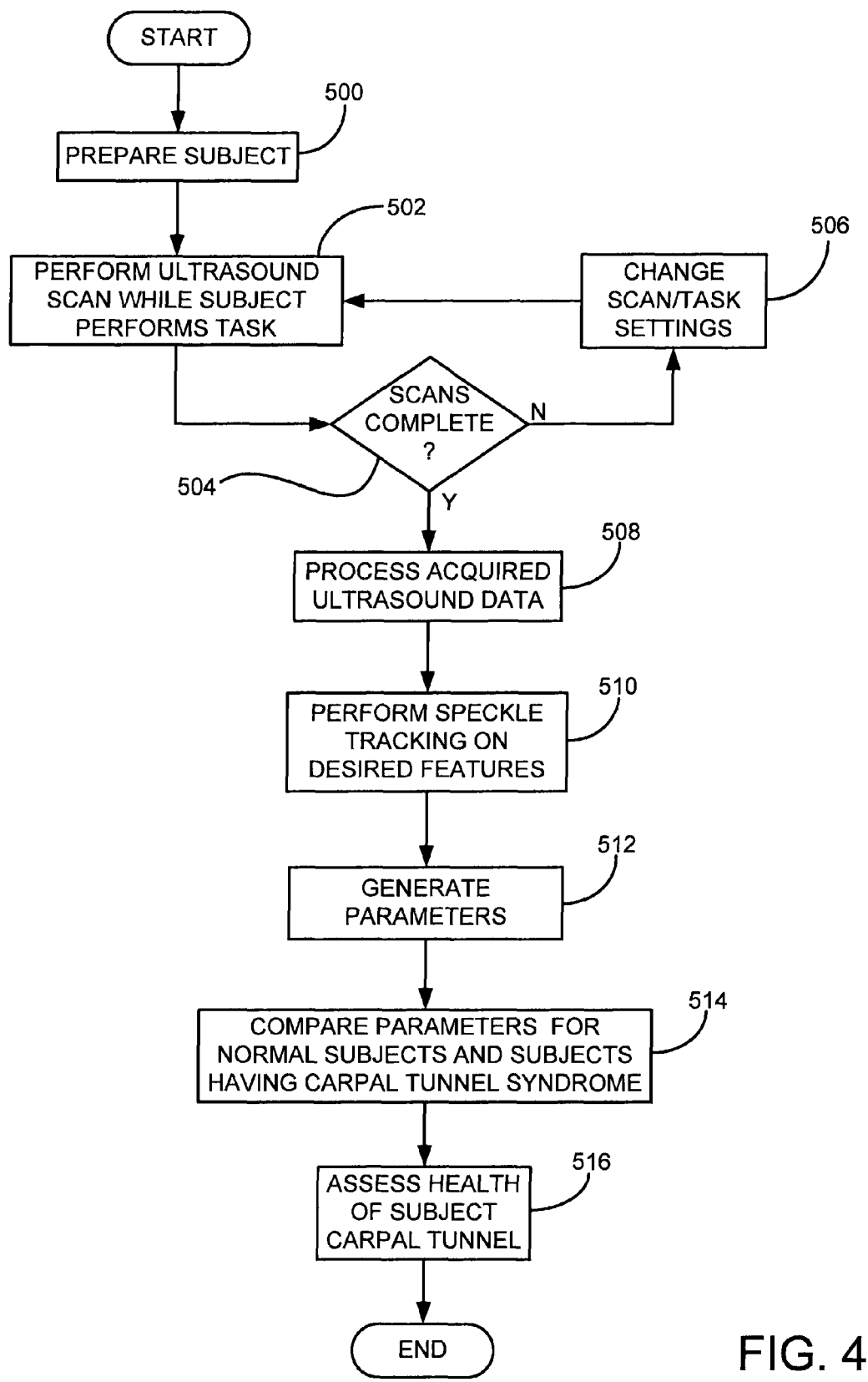
FIG. 4 is a flowchart setting forth the steps of a method for generating risk factors indicative of a subject's risk of developing CTS or SSCT damage using an ultrasonic imaging system in accordance with the present invention.
Figure 5:
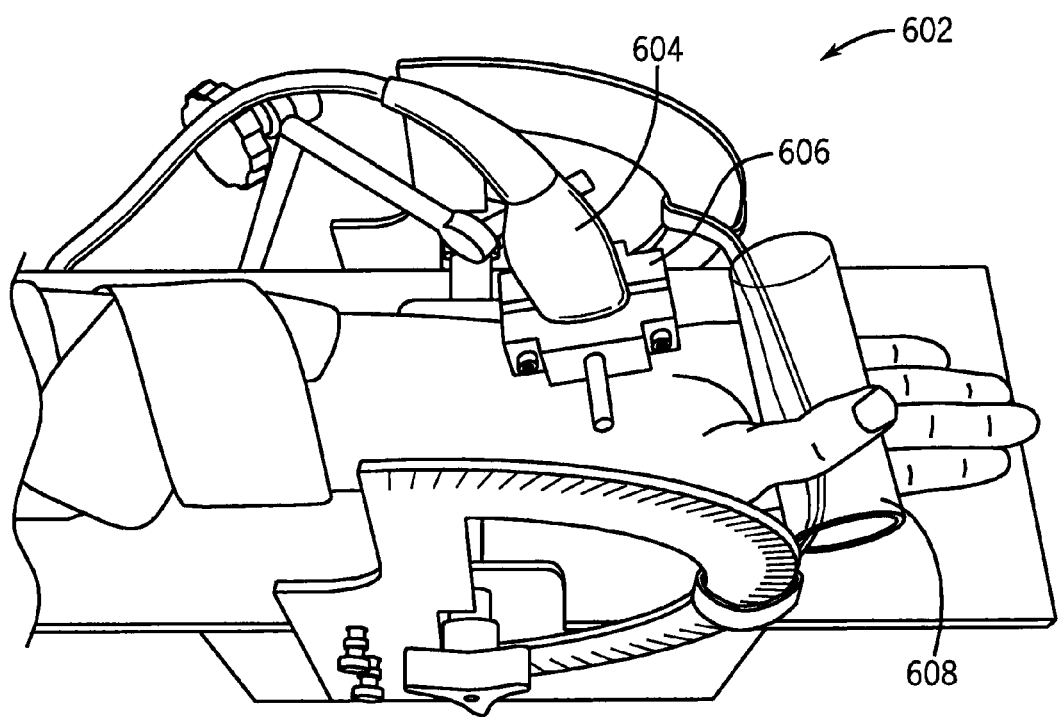
FIG. 5 is a perspective view of an examination apparatus for use with the ultrasonic imaging system of FIG. 1 in accordance with the present invention.

Referring to FIGS. 4 and 5, a general method for ultrasound analysis of CTS risk factors starts and, at process block 500, a subject 600 is prepared for scanning. Specifically, the forearm of the subject is fasted to an examination apparatus, indicated generally at 602, and the transducer head of an ultrasound probe 604 is placed just proximal to the subject's wrist flexion crease and its position is maintained by an ultrasound holding mechanism 606 that is included in the examination apparatus 600. The examination apparatus 600 further includes objects, for example, a gripping devices 608, which may, as illustrated, be a series of acrylic tubes having varying diameters, that a subject manipulates to perform a task, for example, flexing and extending the wrist to grip and release the varying tubes. The examination apparatus 602 is designed to permit desired motion of the subject but restrict undesired motion. It is contemplated that the subject may be trained to perform these tasks repeatedly and consistently, such as using a metronome marking a beat, for example, 0.80 Hz, for flexion and extension.

Referring still to FIG. 4, at process block 502, a time series of ultrasound images is acquired at a specified acquisition rate as the subject performs a task. For example, an ultrasound image may be acquired seventy times each second, providing a 70 Hz image acquisition rate. The tasks generally involve manipulating an object so as to cause flexion and extension of the structures within the carpal tunnel. To improve results and account for any abnormal subject motion, it is contemplated that the subject may repeat the task at least three times while a time series of ultrasound images is acquired. It is further contemplated that imaging is performed using an ultrasound scanner equipped with a 15L8 linear array transducer set to a depth of 20 mm with a 14 MHz image acquisition frequency. At process block 506, the examination apparatus, and the subject's position within the apparatus, are changed so the subject may perform additional tasks. For example, if the subject is flexing and extending their wrist around an acrylic tube, the acrylic tube may be removed from the examination apparatus and replaced with an acrylic tube having a different diameter. This step may further include repositioning the subject within the examination apparatus to allow ultrasound imaging to be performed on the other forearm. At process block 502, the subject performs the new task while a time series of ultrasound images is acquired. The steps in process block 502 and 506 are repeated until, at decision block 504, it is decided that an appropriate number of tasks and ultrasound scans have been performed.

At process block 508, the acquired ultrasound data is preprocessed. Processing includes image compression, truncating the time series of ultrasound images so that only relevant time frames remain, and altering the frame rate of the time series as it is recorded to a computer system. For example, the image acquisition frame rate may be at 70 Hz. However, when operating the ultrasound machine in 'cine' function, where the frames for the previous few seconds are stored in cine memory, regularly, the play speed is slowed down to 37 percent of its original speed. This is because, if the cine images were saved without reduction of the play speed, some of the frames will be truncated during the image saving process. To minimize the flame reduction, the play speed is, thus, slowed down to 37 percent of its original speed.

Figure 6:
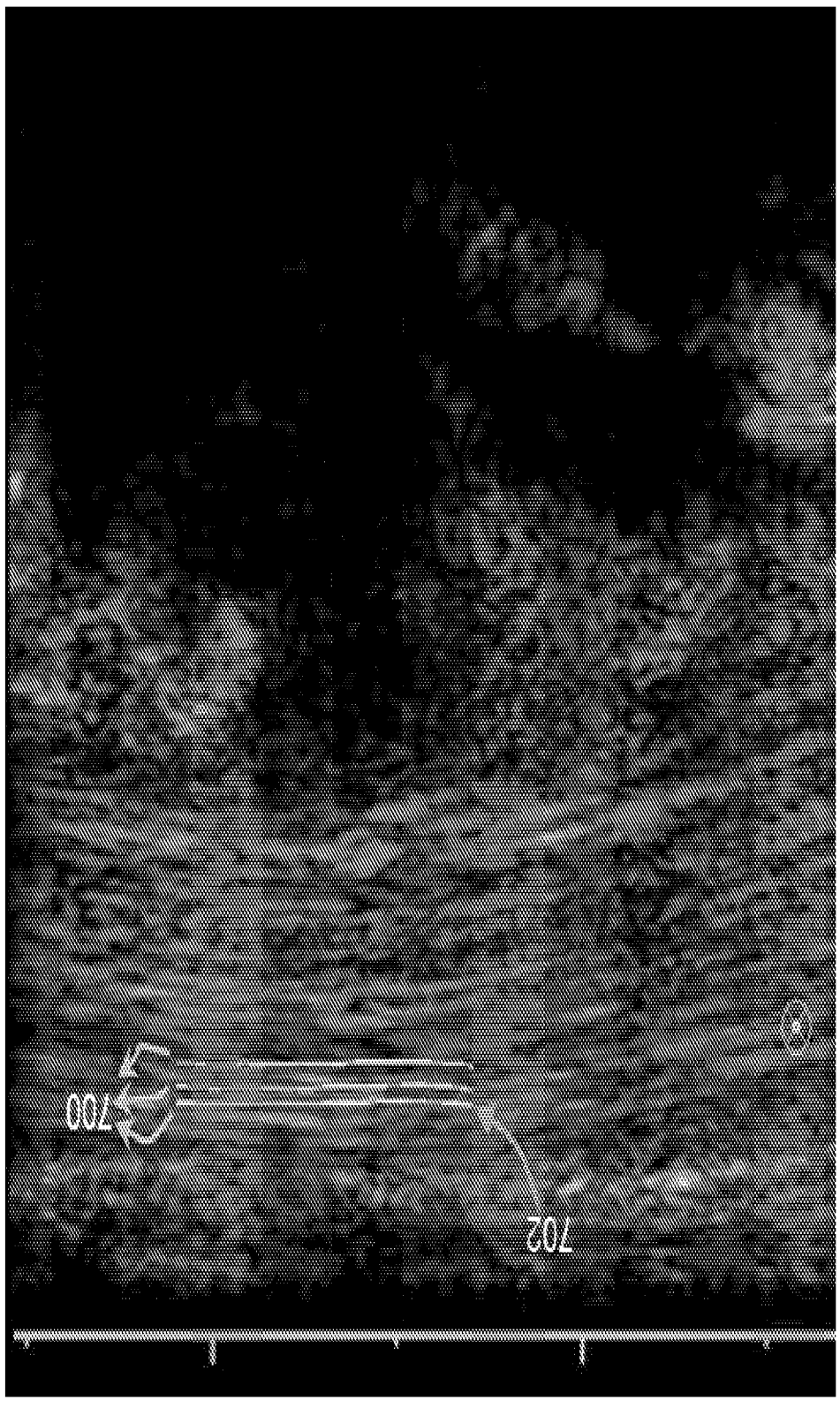
FIG. 6 is an exemplary image showing the tracking of features within the carpal tunnel using methods in accordance with the present invention.

Referring to FIGS. 4 and 6, speckle tracking is performed on the processed time series of ultrasound images at process block 510. Speckle tracking is an angle-independent, two-dimensional dynamic ultrasonic imaging technique that analyzes the motion of a tissue by tracking speckles, which are acoustic signals that arise from the coherent reflection of ultrasound waves off small features, for example, very small cells, in a subject. Speckles are tracked from frame to frame in a time series of ultrasound images with an optimized pattern-matching algorithm, allowing the analysis of dynamic features, for example, the motion of fluid and tissues, by reconstructing the deformation and motion of the speckles.

Anatomical features within the carpel tunnel are tracked by placing tracking markers 700 on speckles within portions of the image containing structures of interest, for example, the flexor digitorum superficialis (FDS) and the SSCT. It is contemplated that three markers may be placed on the FDS tendon tissue speckles, perpendicular to the direction of tendon motion, with a distance between the two furthest markers of one millimeter. The SSCT, a highly echogenic layer at the border of the tendon, is normally thinner than 1 mm and may be tracked by placing markers at the following locations: one at the border between the tendon and the highly echogenic layer; one within the highly echogenic layer; and one at the outer border of the highly echogenic layer. These markers define what is considered a representative segment of the SSCT. Following placement of the markers, speckle tracking software implements a desired optimized pattern-matching algorithm to track the areas bounded by the applied markers. For example, the paths 702 show the motion of the tracking markers 700 through the course of a time series of ultrasound images.

At process block 512, the results of speckle tracking are analyzed and a series of functional parameters characterizing the motion of the tracked structures are generated. Speckle tracking should show a clear difference in the direction of motion of structures within the carpal tunnel between periods of flexion and periods of extension. Therefore, tracking points that most strongly display this difference are selected and analyzed to generate a series of functional parameters characterizing the motion of the tracked structures. For example, velocity and strain time series, may be calculated for the FDS and SSCT. From these time series, the maximum velocities and excursions of the FDS and SSCT may be calculated. Additional functional parameters, such as the maximum velocity ratio, which is the ratio of the SSCT maximum velocity relative to the FDS maximum velocity, and the shear index may be generated. The shear index, which represent SSCT displacement relative to FDS displacement, may be calculated by the following equation:

$$\text{Shear index} = [(\text{Excursion}_{FDS} - \text{Excursion}_{SSCT})/(\text{Excursion}_{FDS})]*100 \text{ percent}$$

Still referring to FIG. 4, following the generation of the functional parameters statistical analysis is performed at process block 514. The statistical analysis compares the functional parameters acquired from a subject to a priori functional parameters obtained from normal subjects and subjects having CTS. At process block 516, the results of the statistical analysis are used to generate risk factors indicative of a subject's risk of developing CTS or SSCT damage. The motion patterns of the SSCT relative to the flexor tendon are known to be different in CTS patient compared to normal subject. This suggests shear condition of the SSCT may be different between CTS patients and normal subjects. By analyzing the difference in the relative motion of SSCT, subjects with a predisposition for CTS, for example, subjects having a normal median nerve but a structurally abnormal SSCT can be identified.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for generating a report indicating a subject's risk for developing a disorder of a carpal tunnel, the system comprising:
   an examination apparatus configured to control motion of the subject through a predetermined set of motions;
   an ultrasound transducer arranged proximate to the subject's carpal tunnel to acquire a time series of medical imaging data of a region of interest including at least a portion of the subject's carpel tunnel; and
   a processor configured to receive the time series of medial medical imaging data and having instructions configured to cause the processor to carry out the steps of:
   i) generating a time series of images from the time series of medial medical imaging data;
   ii) receiving an indication of anatomical features within the time series of medical images;
   iii) analyzing the time series of medical images to determine indicia of acoustic signals arising from coherent reflection of ultrasound waves generated by the transducer from predetermined features within the region of interest and track the determined indicia across the time series of medical images;
   iv) determining a pattern of motion of the determined indicia across the time series of medical images;
   v) generating a series of functional parameters characterizing pattern of motion of the determined indicia across the time series of medical images; and
   vi) using the series of functional parameters, generating a report indicating the subject's risk of developing at least one of carpel tunnel syndrome (CTS) and subsynovial connective tissue (SSCT) damage,
   wherein the anatomical features include a flexor digitorum superficialis (FDS) and the SSCT, and
   wherein step ii) includes receiving a plurality of markers placed on tendon tissue speckles of the FDS, perpendicular to a direction of tendon motion, with a distance between two furthest markers of one millimeter.

2. The system of claim 1 wherein the functional parameters includes motion of fluid and tissues in the region of interest and step v) includes reconstructing deformation and motion of the determined indicia.

3. The system of claim 1 wherein step ii) includes receiving a plurality of markers placed on the SSCT at a plurality of positions including a border between a tendon and a highly echogenic layer, within the highly echogenic layer, and an outer border of the highly echogenic layer.

4. The system of claim 1 wherein the functional parameters include velocity, maximum velocity, maximum velocity ratio, strain, excursions, and shear index for the FDS and SSCT.

5. The system of claim 4 wherein the shear index represents SSCT displacement relative to FDS displacement, and is calculated using the following equation:

$$\text{Shear index} = [(\text{Excursion}_{FDS} - \text{Excursion}_{SSCT}/\text{Excursion}_{FDS})]*100 \text{ percent}.$$

6. The system of claim 1 wherein step vi) includes comparing the series of functional parameters to a priori functional parameters acquired from normal subjects and subjects known to have CTS.

7. The system of claim 6 wherein the comparing includes performing a statistical analysis to generate risk factors indicative of risk of developing at least one of CTS and SSCT damage.

8. The system of claim 1 wherein the examination apparatus includes a gripping device and wherein predetermined set of motions includes flexing and extending a wrist of the subject to grip and release the gripping device.

9. The system of claim 8 wherein the gripping device is configured to be interchangeable with a variety of gripping devices having varying physical and operational parameters.

10. A method for analyzing a subject's carpal tunnel using an ultrasonographic imaging system, the method comprising:

a) arranging a subject within an examination apparatus;
b) acquiring a plurality of time series of ultrasound images of the subject's carpal tunnel as the subject performs a series of tasks controlled by the examination apparatus;
c) performing speckle tracking on the time series of ultrasound images;
d) analyzing the speckle tracking to determine a plurality of functional parameters of the subject;
e) performing statistical analysis to compare the functional parameters of the subject with a priori functional parameters from normal subjects and subjects having carpal tunnel syndrome; and
f) generating risk factors indicative of the subject's risk of developing carpal tunnel syndrome (CTS) or subsynovial connective tissue (SSCT) damage based on the comparison performed in step e),
wherein the subject's carpal tunnel include a flexor digitorum superficialis (FDS) and the SSCT, and
wherein step b) includes receiving a plurality of markers placed on tendon tissue speckles of the FDS, perpendicular to a direction of tendon motion, with a distance between two furthest markers of one millimeter.

11. The method of claim 10 wherein step a) further includes at least one of disposing the subject's wrist within the examination apparatus to allow the subject to manipulate the examination apparatus to form a task.

12. The method of claim 10 wherein step c) further includes tracking the flexor digitorum superficialis (FDS) and the SSCT.

13. The method of claim 10 wherein step d) further includes determining a maximum velocity and maximum velocity ratio of the FDS and the SSCT, excursions of FDS and SSCT, and a shear index representing the SSCT excursion relative to the FDS excursion.

* * * * *

UNITED STATES PATENT AND TRADEMARK OFFICE
CERTIFICATE OF CORRECTION

PATENT NO. : 8,795,181 B2  
APPLICATION NO. : 13/130210  
DATED : August 5, 2014  
INVENTOR(S) : Chunfeng Zhao et al.

Page 1 of 1

It is certified that error appears in the above-identified patent and that said Letters Patent is hereby corrected as shown below:

In the Claims

Claim 1, Column 8, line 1-2 "of medial medical" should be -- of medical --  
Claim 1, Column 8, line 5 "medial medical" should be -- medical --

Signed and Sealed this  
Twenty-fourth Day of February, 2015

Michelle K. Lee  
*Deputy Director of the United States Patent and Trademark Office*